(12) United States Patent
Lim

(10) Patent No.: US 6,841,029 B2
(45) Date of Patent: Jan. 11, 2005

(54) SURFACE MODIFICATION OF EXPANDED ULTRA HIGH MOLECULAR WEIGHT POLYETHYLENE (EUHMWPE) FOR IMPROVED BONDABILITY

(75) Inventor: Florencia Lim, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/400,809

(22) Filed: Mar. 27, 2003

(65) Prior Publication Data

US 2004/0191442 A1 Sep. 30, 2004

(51) Int. Cl.[7] .............................. C09J 5/02; B32B 31/20; B44C 1/22; C03C 15/00; C03C 25/68
(52) U.S. Cl. ................................ 156/308.6; 156/308.4; 156/308.2; 156/229; 156/191; 156/187; 156/281; 216/34; 216/83
(58) Field of Search ........................... 156/244.11, 153, 156/184, 1.87, 191, 192, 297, 299, 300, 155, 244.23, 281, 187, 229, 292, 308.2, 308.4, 308.6; 264/632; 216/34, 41, 83, 95; 427/322, 307; 604/103; 606/194, 96.01

(56) References Cited

U.S. PATENT DOCUMENTS 4,655,769 A    4/1987  Zachariades 5,749,852 A  *  5/1998  Schwab et al. .......... 604/103.01
5,922,161 A     7/1999  Wu et al.
6,010,480 A  *  1/2000  Abele et al. ............ 604/103.06
6,213,975 B1    4/2001  Laksin
6,344,045 B1    2/2002  Lim et al.
6,428,506 B1    8/2002  Simhambhatla et al.
6,482,173 B2   11/2002  Laksin
2003/0211258 A1 * 11/2003 Sridharan et al. .......... 428/35.2
2004/0062890 A1    4/2004 Wang et al.

FOREIGN PATENT DOCUMENTS

WO        WO 91/01210        2/1991

* cited by examiner

Primary Examiner—Michael C. Miggins
(74) Attorney, Agent, or Firm—Fulwider Patton Lee & Utecht LLP

(57) ABSTRACT

A balloon catheter and a method of making the balloon catheter, having a balloon which is bonded to an elongated shaft, and which has a first layer and a second layer and an improved bond between the balloon and the shaft. One aspect of the invention is directed to a balloon in which the balloon first layer includes eUHMWPE and has at least a section that has been oxidized with a chromic acid solution to provide improved bondability.

13 Claims, 2 Drawing Sheets

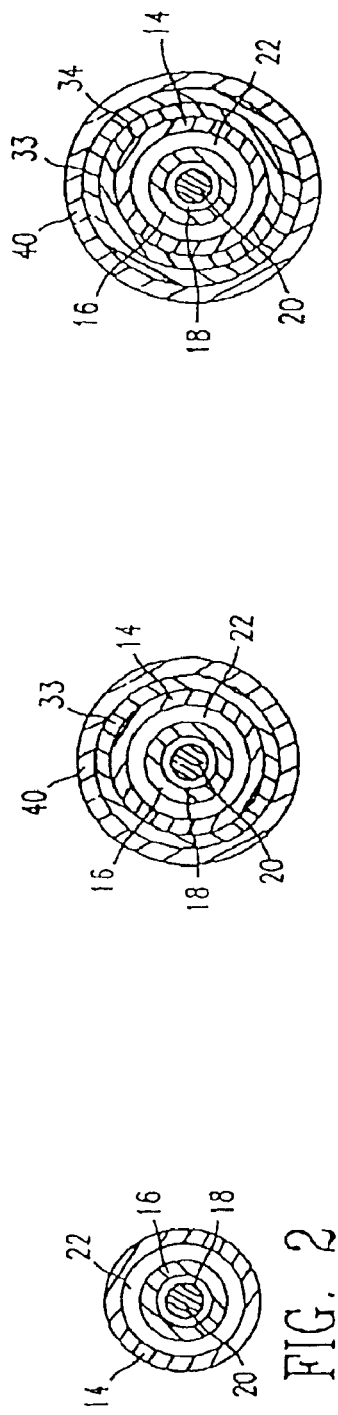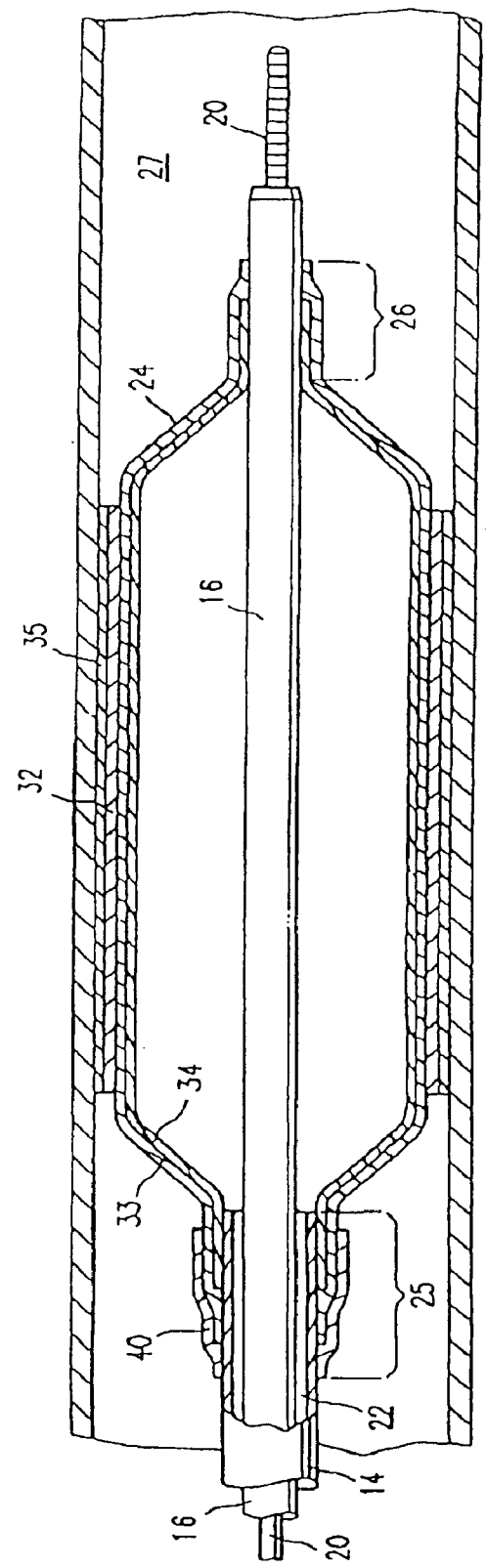

SURFACE MODIFICATION OF EXPANDED ULTRA HIGH MOLECULAR WEIGHT POLYETHYLENE (EUHMWPE) FOR IMPROVED BONDABILITY

BACKGROUND OF THE INVENTION

This invention generally relates to medical devices, and particularly to intracorporeal devices for therapeutic or diagnostic uses, such as balloon catheters. In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated blow molded balloon forms wings which are folded around the catheter shaft prior to inflation of the balloon in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

A catheter balloon formed of expanded ultra high molecular weight polyethylene (eUHMWPE) has been suggested. However, eUHMWPE has proven difficult to bond to balloon liner materials and to catheter shaft materials.

It would be a significant advance to provide a catheter balloon, or other medical device component, with improved performance and bondability.

SUMMARY OF THE INVENTION

This invention is directed to a balloon catheter and a method of making the balloon catheter, having a balloon which is bonded to an elongated shaft, and which has a first layer and a second layer and an improved strong bond between the balloon and the shaft. One aspect of the invention is directed to a balloon in which at least one of an inner surface and outer surface of the first layer has at least a section with a modified surface formed by a chromic acid solution treatment. The modified surface improves the strength of the bond between the first layer and the second layer or liner and with the catheter shaft.

A balloon catheter of the invention generally comprises an elongated shaft having a proximal end, a distal end, and at least one lumen, and a balloon on a distal shaft section with an interior in fluid communication with the at least one lumen of the shaft. The balloon has a proximal skirt section bonded to the shaft, a distal skirt section bonded to the shaft, an inflatable section therebetween, and first and second layers extending from the proximal skirt section to the distal skirt section. In a presently preferred embodiment, the first layer is an outer layer relative to the second layer, although the first layer may alternatively be an inner layer relative to the second layer. In one embodiment, the outer (e.g., first) layer extends beyond the ends of the inner (e.g., second) layer. Specifically, in one embodiment, the first layer has a proximal end section and a distal end section, which extend beyond the second layer of the balloon and onto the shaft, so that the proximal and distal end sections of the first layer are in contact with and bonded to the shaft. The catheter shaft typically comprises an outer tubular member defining the inflation lumen, and an inner tubular member defining a guidewire lumen extending at least within a distal shaft section, with the balloon proximal skirt section bonded to a distal portion of the outer tubular member and the balloon distal skirt section bonded to a distal portion of the inner tubular member. However, a variety of suitable catheter configurations can be used as are conventionally known, including dual lumen designs. The balloon catheter can be an over-the-wire type catheter with an guidewire lumen extending from the proximal to the distal end of the catheter, or alternatively a rapid exchange type catheter with a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter. A balloon catheter of the invention can be configured for use in a variety of applications including coronary and peripheral dilatation, stent delivery, drug delivery, and the like.

In one embodiment, the first layer comprises a polyolefin, preferably an ultra high molecular weight polyolefin (UHMWPO) such as ultra high molecular weight polyethylene (UHMWPE). It is presently preferred that the polyolefin be porous. For example, UHMWPE such as expanded ultra high molecular weight polyethylene (eUHMWPE) typically is porous. The first layer may also be a porous material including porous polyolefin, porous polyethylene, porous polypropylene, and expanded UHMWPO. In one embodiment, the porous material, such as UHMWPE or eUHMWPE, typically will have a node and fibril microstructure and are not melt extrudable. The node and fibril microstructure, when present, is produced in the material using conventional methods eUHMWPE is preferably made as a thin tape, and it is presently preferable to form a balloon layer by winding the tape into a tube, sintering the tube in a furnace, stretching the tube and sintering the tube for a second time, and compacting the tube and sintering the tube for a third time to provide the final balloon.

With regard to the material, the expanded UHMWPE in one embodiment is formed of basic or non-expanded UHMWPE, a polyethylene with a molecular weight typically between about 2 million and about 10 million grams/mole, that has been expanded or drawn to deform the UHMWPE into a microporous material exhibiting an oriented microstructure of nodes interconnected by fibrils. In this embodiment, the expanded UHMWPE may have a porosity of about 20% to about 90%. Examples of expanded, microporous UHMWPE having a node and fibril microstructure, and a suitably high orientation with an anisotropic structure or at least significant anisotropy in the structure are described in PCT International Publication No. WO 91/01210 (Evans), incorporated by reference herein in its entirety. As described in WO 91/01210, such UHMWPE materials may exhibit a negative Poisson ratio.

In one embodiment, at least a section of the balloon first layer has been oxidized and etched with a chromic acid solution. The oxidized and etched section of the first layer typically extends along at least a portion of the proximal skirt section, although the oxidized and etched section of the first layer may extend along the distal skirt section or along both the proximal and distal skirt sections. In one embodiment the oxidized and etched section extends along the entire length of an inner surface of the first layer from the proximal to the distal end thereof. The oxidized and etched sections of the first layer extend along at least part of the inner surface of the end sections of the outer layer which are in contact with and bonded to the shaft. Additionally, at least a section, and preferably a proximal and/or a distal end section, of an outer surface of the first layer is oxidized and etched in one embodiment. The oxidized and etched outer surface of the first layer is typically bonded to another component of the catheter such as a sleeve member, which may be a polymeric sleeve or a metallic band, on the end section of the first layer. For example, in one embodiment, the balloon catheter includes a sleeve member which preferably provides a higher balloon seal rupture pressure (i.e., a high strength bond between the balloon and shaft), and which is bonded to the shaft and to a portion of an oxidized inner or an oxidized outer surface of the first layer. The outer surface of the first layer may also be entirely oxidized and etched with a chromic acid solution, so that a hydrophilic coating will have a strong bond to the outer surface. The hydrophilic coating provides added lubricity to the balloon.

The oxidized and etched surface is the result of a chemical reaction between the polymeric material forming the first layer and the chromic acid solution. The chromic acid solution oxidizes and etches the surface of the eUHMWPE material without affecting the bulk properties of the eUHMWPE, and the chromic acid solution leaves the eUHMWPE clear of any discoloration. In one embodiment, the total wall thickness of a balloon is between 0.0051–0.023 cm (0.0020–0.0090 inch), and the thickness of the resulting oxidized layer extends from the surface of the first layer to a depth of about 25 to 100 microns. While treating the first layer with the chromic acid solution, a sheath may first be placed over the outer surface of the first layer to prevent oxidation of the outer surface if so desired. The etched surface is preferably heat fusion and/or adhesive bonded to an adjacent member. In one embodiment, a mechanical engagement between the oxidized and etched surface and the shaft improves the strength and durability (i.e., fatigue resistance) of the bond, where, for example, an outer member is provided which clamps or crimps down onto the balloon at the location of the bond between the balloon and the shaft.

A method of making a balloon catheter which embodies features of the invention generally includes positioning a balloon having an inner layer and an outer layer over a distal section of a catheter shaft, the outer layer having an inner surface which has been at least partially treated with a chromic acid solution to oxidize and etch the surface. The proximal and distal end sections of the balloon are then bonded to the shaft, as for example by heat fusion and/or adhesive bonding, to form the balloon catheter.

The balloon catheter of the invention has an improved bond between the balloon and the catheter shaft, and an improved bond between the first layer of the balloon and the second layer. In a first embodiment, the improved bond is due at least in part to an oxidized and etched section of the first layer of the balloon. The oxidized and etched section provides a strong bond between the oxidized and etched surface and an adjacent catheter component, with improved manufacturability. These and other advantages of the invention will become more apparent from the following detailed description and accompanying exemplary figures.

BRIEF DESCRIPTION OF THE DRAWINGS

FIG. 2 is a transverse cross sectional view of the balloon catheter shown in FIG. 1, taken along line 2—2.

FIG. 3 is a transverse cross sectional view of the balloon catheter shown in FIG. 1, taken along line 3—3.

FIG. 4 is a transverse cross sectional view of the balloon catheter shown in FIG. 1, taken along line 4—4.

FIG. 5 illustrates the balloon catheter of FIG. 1, with the balloon in an inflated configuration to expand the stent within the patient's body lumen.

DETAILED DESCRIPTION OF THE PREFERRED EMBODIMENTS

Figure 1:
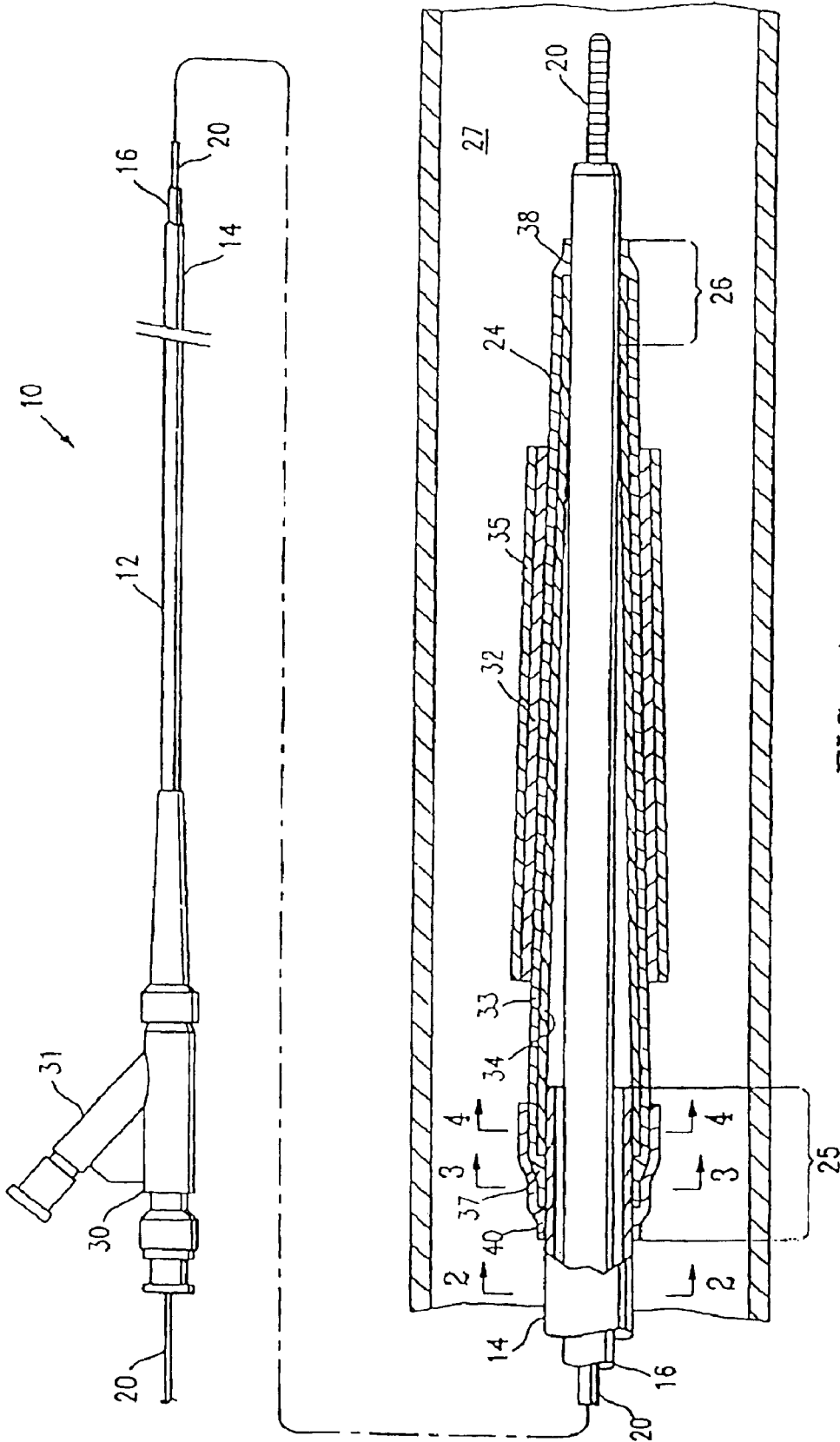
FIG. 1 is an elevational view, partially in section, of a stent delivery balloon catheter embodying features of the invention.

FIG. 1 illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section of the distal end of the catheter shown in FIG. 1, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that the balloon interior is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1, the balloon 24 is illustrated prior to complete inflation thereof, with an expandable stent 32, with stent cover 35, mounted on the working length of the uninflated balloon 24 for implanting within a patient's body lumen 27. The distal end of catheter 10 may be advanced to a desired region of the patient's body lumen 27 in a conventional manner, the balloon 24 inflated to expand covered stent 32, and the balloon deflated, to implant the covered stent 32 in the body lumen 27.

Balloon 24 has an outer layer 33 and an inner layer 34, extending from the proximal skirt section 25 to the distal skirt section 26 of the balloon 24. The inner surface of the outer layer 33 is preferably bonded to the inner layer 34, as for example by fusion bonding or adhesive bonding. The balloon 24 is preferably bonded to the shaft 12 by fusion and/or adhesive bonding. Conventional adhesives such as light-cured (e.g., Dymax 204) and cyanoacrylates (e.g., Loctite 4011) may be used to bond layers 33, 34 to the shaft 12 at the proximal skirt section 25 and distal skirt section 26 of the balloon 24. In the embodiment illustrated in FIG. 1, the outer layer 33 of the balloon 24 has a proximal end section 37 proximal to the inner layer 34 and bonded to the outer tubular member 14, and a distal end section 38 distal to the inner layer 34 and bonded to the inner tubular member 16. The end sections 37, 38 of the outer layer 33, together with end sections of the inner layer 34 bonded to the shaft 12, form the proximal and distal skirt sections 25, 26, respectively. The length of the sections of each layer 33 and 34 of the balloon 24 secured to the shaft to form the proximal and distal skirt sections 25, 26 are preferably minimized. Thus, the proximal and distal skirt sections 25, 26 preferably have a length about equal to the minimal length required to provide a suitably strong bond between the balloon 24 and the shaft 12. The proximal end section and the distal end section of the inner layer 34 bonded to the shaft have a length of typically about 1 to about 5 mm, and the proximal end section and the distal end section of the outer layer 33 extending beyond the inner layer 34 and bonded to the shaft have a length of typically about 1 mm to about 4 mm, preferably about 1 mm to about 2 mm, for a balloon 24 having a length of about 8 to about 60 mm and a nominal outer diameter of about 2 to about 18 mm. Although the proximal skirt section 25 is illustrated with a longer length than the distal skirt section, in alternative embodiments, the length of the skirt sections 25, 26 may be equal, or the proximal skirt section 25 may be shorter than the distal skirt section 26.

Additionally, in the embodiment of FIG. 1, a proximal outer sleeve member 40 has a distal portion bonded to an outer surface of the outer layer 33 and a proximal portion located proximal to the outer layer 33 and bonded to the outer tubular member 14. The sleeve member 40 preferably increases the rupture pressure of the bond between the balloon and shaft (and typically by at least about 100 psi), and preferably increases the fatigue resistance of the bond. In the embodiment of FIG. 1, the proximal sleeve member 40 comprises a polymeric material. The sleeve member 40 is preferably formed of polyurethanes, although it may be formed of a variety of suitable polymeric materials including polyamides such as nylon or polyether block amide (PEBAX), and may include radiopaque material incorporated into the polymeric matrix for use as a radiopaque marker for visualizing the catheter under fluoroscopy in the patient's body lumen. The sleeve member 40 is preferably bonded by fusion bonding, although it may alternatively be adhesively bonded. In alternative embodiments, a proximal sleeve member in the form of a metallic band (not shown) is mounted on at least a portion of the proximal skirt section 25 of the balloon 24. The metallic proximal sleeve member may be formed of a radiopaque material for use as a radiopaque marker, such as gold or a platinum-iridium alloy, or nonradiopaque materials. The metallic proximal sleeve member is typically crimped onto the outer surface of the outer layer 33 at the proximal skirt section, although it may alternatively be secured using an adhesive. The metallic proximal sleeve member reinforces the bond between the balloon and the shaft, to increase the durability of the bond after multiple inflations of the balloon. Thus, a metallic proximal sleeve member crimped onto the proximal skirt section 25 increased the durability of the bond to the shaft, so that the balloon can be inflated at the relatively high inflation pressure (i.e., 18 atm or more) multiple times without the proximal skirt section bond failing. For example, with the metallic sleeve member thereon, the proximal or distal skirt section 25, 26 typically does not fail before about 20 to about 50 inflations at the relatively high inflation pressure, whereas the skirt sections 25, 26 fail after about 1 to about 19 inflations in the absence of the metallic proximal sleeve member. Although not illustrated in FIG. 1, a distal sleeve member may be provided at the distal skirt section 26 of the balloon, similar to the polymeric or metallic proximal sleeve members discussed above.

In the embodiment of FIG. 1, the outer layer 33 of the balloon 24 has an inner surface which is oxidized and etched along at least a section of the length of the outer layer 33. In one embodiment, the oxidized and etched section of the inner surface of the outer layer 33 extends along the entire length of the inner surface of the outer layer 33, to provide a secure bond to the shaft and to the inner layer 34. However, in alternative embodiments, the oxidized and etched section of the inner surface of outer layer 33 extends along less than the entire length of the outer layer 33, and is therefore longitudinally adjacent to a section of the inner surface of the outer layer 33 which is not etched. For example, in one embodiment the oxidized and etched sections of the inner surface of the outer layer 33 extend along the proximal and distal skirt sections 25, 26 (i.e., along the sections of the outer layer 33 which are bonded to the shaft and which are bonded to the end sections of the inner layer bonded to the shaft). In one presently preferred embodiment, all portions of the outer layer 33 that are bonded to another material, such as the catheter shaft and the inner layer, are oxidized and etched to provide a stronger bond.

In one embodiment, at least a section of the outer surface of the outer layer 33 of the balloon 24 is oxidized and etched, such as a proximal section of the outer layer 33 which is bonded to the proximal sleeve member 40. Additionally, an outer surface of a distal portion of the outer layer 33 may similarly be oxidized and etched in the embodiment in which including a distal sleeve member or other component such as a radiopaque marker on the outer surface of the outer layer 33 at the balloon distal skirt section 26. In another embodiment, the outer surface of the central, inflatable section of the outer layer 33 (having the stent 32 thereon in FIG. 1) is not oxidized and etched, and the oxidized and etched outer surface of the outer layer 33 is thus typically adjacent to a section of the outer surface of the outer layer 33 which is not oxidized and etched. In yet another embodiment, the entire outer surface of the outer layer 33 is oxidized and etched in preparation for attaching a lubricious coating such as a hydrophilic coating.

In a presently preferred embodiment, the oxidized and etched inner and outer surfaces of the outer layer 33 are prepared using a chromic acid solution. The outer layer 33 is etched by exposing the polymeric tube which forms the outer layer 33 to the chromic acid solution, as for example by dipping the polymeric tube in a container of chromic acid solution. Sections of the polymeric tube may be masked to prevent oxidizing and etching of the sections before dipping the tube in the solution. For example, in order to prevent oxidizing and etching of all or part of the outer surface of the polymeric tube forming outer layer 33, a polymeric covering such as a polymeric sheath with a length equal to or less than the length of the polymeric tube, is placed on the polymeric tube, tightly fitting thereon, before the tube is dipped in the chromic acid solution. The sheath prevents the etching solution from contacting the outer surface of the polymeric tube covered by the sheath. Similarly, a tightly fitting mandrel may be used in the inner lumen of the polymeric tube to mask sections of the inner surface of the polymeric tube. After removal from the chromic acid solution, the polymeric tube is typically dipped or otherwise thoroughly rinsed with dilute nitric acid and deionized water to remove any residual chromic acid from the polymeric tube. The resulting oxidized and etched tube is then completely dried.

For example, in one embodiment the outer layer 33 is oxidized and etched using the following process. About 100 ml of about 50% CrO3 in water, which results in about 22–26% chromium, with sodium thiosulfate Na2S2O3, available from Sigma-Aldrich under the trade name Chromerge, is poured into one gallon of sulfuric acid and heated to about 70° C. The outer layer 33 is formed into a tube having a length of about 8 cm and is tightly fit into a polymeric sheath (preferably formed of PTFE, and both ends are flared to facilitate the chemical solution flow therein, or if it is desired to have the outer surface of the tube oxidized and etched, no sheath is used. The entire tube (with or without sheath) is dipped into the chromic acid solution for about 2 to 30 minutes. The tube is removed from the solution and drained, and then rinsed thoroughly with diluted nitric acid and deionized water to remove any residual chromic acid that may still be on the tube. The tube is then dried in an oven or nitrogen gas stream, followed by drying the tube in a vacuum oven if needed.

The presently preferred method includes submerging the tube into the chromic acid solution at 70° C. for 2 to 30 minutes, however, the chromic acid solution may be heated anywhere from 25° C.–79° C. In one embodiment at 70° C., it is sufficient to leave the tube in the solution for about 2 to 30 minutes. At lower temperatures, the tube will have to be submerged in the chromic acid solution for a longer period of time, and at temperatures above 70° C., the tube will be submerged in the solution for less than 2 minutes.

The chromic acid treatment can be used on any polyolefin, including eUHMWPE. As a result of the treatment, the surface of the eUHMWPE will be etched and oxidized by creating a carboxylic acid group among other oxide groups. The treatment etches the surface of the polyolefin by "roughening" the surface of the material to provide a higher surface area without changing any chemical properties. Further, the treatment of eUHMWPE with chromic acid leaves the material clear of any discoloration. The thickness of the resulting oxidized layer is between about 25 and 100 microns, and therefore the bulk properties of the eUHMWPE are not affected. The tensile and rupture properties of the treated eUHMWPE is expected to be similar to the untreated eUHMWPE. Rupture strength of a balloon with a wall thickness less than 0.006 inch is expected to be no less than 26 atm. As a result of the chromic acid treatment, a stronger bond between the eUHMWPE balloon layer and the polyamide (such as Nylon and pebax) and polyurethane shaft materials can be made. Also, a stronger bond between the eUHMWPE balloon layer and the inner layer or liner is produced. The bonding strength of the polyolefin is increased sufficiently by the chromic acid treatment that no other functional groups, such as amines, need to be attached to the surface.

The oxidized and etched tubular outer layer 33 of the balloon 24, formed of a porous polymeric material such as for example eUHMWPE, is positioned on an outer surface of the tubular inner layer 34, either before or after the inner layer 34 is bonded to the shaft (i.e., to the outer and inner tubular members 16, 14). For example, to form a fusion bond, heat is applied at the proximal and distal end sections of the inner tubular layer 34, to melt the polymeric material of the shaft 12 and the polymeric material of the inner tubular layer 34 at least at the interface thereof, and fusion bond the proximal and distal end sections of the inner tubular layer 34 of the balloon 24 to the outer and inner tubular members 14, 16, respectively. Specifically, the ends of the balloon, in position against the catheter shaft and typically with shrink tubing therearound, are heated to a temperature at or above the melting temperature of the polymers, and the polymeric material allowed to cool to form a fusion bond.

During a medical procedure, the balloon 24 is typically inflated to a working pressure of about 6 atm to about 25 atm, preferably about 6 atm to about 20 atm. The balloon is inflatable within the working pressure range without the skirt sections 25, 26 of the balloon 24 failing. In the embodiment of FIG. 1, the balloon 24 bonded to the shaft, and including proximal sleeve member 40, preferably has a rupture pressure at the proximal fusion/adhesive bond of at least about 210 psi, and more specifically of about 300 to about 400 psi.

In a presently preferred embodiment, the balloon outer layer 33 of the balloon catheter 10 comprises a porous polymeric material, and preferably a microporous polymeric material having a node and fibril microstructure, such as eUHMWPE, and the inner layer 34 is formed of a polymeric material preferably different from the polymeric material of the outer layer 33. Preferably, the length of outer layer 33 in contact with inner layer 34 is bonded thereto, and preferably by heat fusion bonding. Inner layer 34 limits or prevents leakage of inflation fluid through the microporous eUHMWPE to allow for inflation of the balloon 24, and is preferably an elastomeric material to facilitate deflation of the balloon 24 to a low profile deflated configuration. The inner layer 34 is preferably formed of an elastomeric material, including dienes, polyurethanes, silicone rubbers, polyamide block copolymers, and the like. The elastomeric material forming layer 34 may consist of a separate layer which neither fills the pores nor disturbs the node and fibril structure of the eUHMWPE layer 33, or it may at least partially fill the pores of the eUHMWPE layer 33.

The eUHMWPE layer 33 is formed according to conventional methods, and is preferably made as a thin tape with a width and thickness ranging from about 3–5 mm and 0.0005 to 0.003 inch, respectively. The eUHMWPE tape can be wound around a mandrel into a tube, that will eventually form the shape of the balloon. Preferably, the polymeric material has the desired microstructure (e.g., porous and/or node and fibril) before being wound onto the mandrel. The tape of eUHMWPE polymeric material is wrapped spirally along a length of the mandrel, to form one or more layers, and preferably about two to about five layers, of wrapped material. The multiple layers of eUHMWPE are typically heated to fuse the layers together. Further processing of the eUHMWPE tube typically includes stretching the eUHMWPE tube, sintering, compacting, and sintering again, to provide the desired properties such as the desired dimension, and dimensional stability (i.e., to minimize changes in length occurring during inflation of the balloon). The completed eUHMWPE layer 33 is then oxidized and etched in accordance with the invention and bonded to or otherwise combined with elastomeric liner 34 either before or after layer 34 is bonded to the shaft.

The dimensions of catheter 10 are determined largely by the size of the balloon and guidewire to be employed, the catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), and the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and a wall thickness of about 0.004 to about 0.008 inch (0.01 to 0.02 cm). The overall length of the catheter 10 may range from about 100 to about 150 cm, and is typically about 143 cm. Preferably, balloon 24 has a length about 0.8 cm to about 6 cm, and an inflated working diameter of about 2 to about 10 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. In the embodiment illustrated in FIG. 1, the outer and inner tubular members 14, 16 are each formed of a single-layered, uniform polymeric member. However, it should be understood that in alternative embodiments, one or both of the outer and inner tubular members 14, 16 may be a multilayered or blended polymeric member. Although the shaft is illustrated as having an inner and outer tubular member, a variety of suitable shaft configurations may be used including a dual lumen extruded shaft having a side-by-side lumens extruded therein. Similarly, although the embodiment illustrated in FIG. 1 is an over-the-wire stent delivery catheter, balloons of this invention may also be used with other types of intravascular catheters, such as rapid exchange type balloon catheters.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:

1. A method for forming a balloon for an intraluminal catheter, comprising:
    a) forming a material including expanded high molecular weight polyolefin into a balloon shape having an inner surface and an outer surface to form a first layer;
    b) treating at least a portion of the first layer with a chromic acid solution; and
    c) providing a tubular polymeric second layer and attaching the second layer directly to a treated portion of at least one of the inner surface and outer surface of the first layer by fusion bonding.

2. The method of claim 1, further comprising rinsing the material after the chromic acid solution treatment.

3. The method of claim 1, further comprising drying the material before attaching the second layer.

4. The method of claim 1, wherein treating the first layer with a chromic acid solution at about 25° C. to about 79° C. for a sufficient amount of time.

5. The method of claim wherein 1, wherein c) comprises attaching the second layer to the inner surface of the first layer between a proximal skirt section and a distal skirt section of the first layer.

6. The method of claim 1, further comprising placing a sheath over the outer surface of the first layer before the chromic acid treatment, wherein only the inner surface of the first layer is treated with chromic acid solution.

7. The method of claim 1, wherein forming the porous polyolefin material into a balloon shape includes winding the material into a tube, sintering the tube, stretching the tube and sintering the tube a second time, and compacting the tube and sintering the tube a third time.

8. The method of claim 1, wherein the material of the first layer includes expanded ultra high molecular weight polyethylene.

9. A method of making a balloon catheter, comprising:
    a) positioning a balloon having an inner layer and an outer layer over a distal section of a catheter shaft, the outer layer having an inner surface and an outer surface, with at least a portion of the inner surface being oxidized from a chromic acid treatment; and
    b) bonding proximal and distal end sections of the balloon to the catheter shaft to form the balloon catheter having at least a portion of the oxidized inner surface of the outer layer of the balloon bonded directly to the shaft by fusion bonding and wherein the outer layer of the balloon is expanded ultra high molecular weight polyolefin.

10. The method of claim 9, wherein the outer layer of the balloon is a porous material selected from the group consisting of porous polyolefin, porous polyethylene, porous polypropylene, and expanded ultra high molecular weight polyethylene.

11. The method of claim 9, wherein the outer layer of the balloon is expanded ultra high molecular weight polyethylene.

12. The method of claim 9, further comprising oxidizing the outer surface of the outer layer with the chromic acid treatment and disposing a hydrophilic coating directly onto the oxidized outer surface.

13. The method of claim 9, including bonding at least a portion of the inner layer to the catheter shaft.

* * * * *